(12) United States Patent
Nakatani (10) Patent No.: US 9,595,420 B2
(45) Date of Patent: Mar. 14, 2017

(54) METHOD FOR PREPARING LAMELLA

(71) Applicant: HITACHI HIGH-TECH SCIENCE CORPORATION, Tokyo (JP)

(72) Inventor: Ikuko Nakatani, Tokyo (JP)

(73) Assignee: HITACHI HIGH-TECH SCIENCE Corporation (JP)

( * ) Notice: Subject to any disclaimer, the term of this patent is extended or adjusted under 35 U.S.C. 154(b) by 0 days.

(21) Appl. No.: 13/706,426

(22) Filed: Dec. 6, 2012

(65) Prior Publication Data

US 2013/0175446 A1 Jul. 11, 2013

(30) Foreign Application Priority Data

Dec. 8, 2011 (JP) ................................. 2011-268875

(51) Int. Cl.
| | | |
|---|---|---|
| *H01J 37/304* | (2006.01) | |
| *G01N 1/28* | (2006.01) | |
| *H01J 37/26* | (2006.01) | |
| *G01N 23/225* | (2006.01) | |
| *H01J 37/20* | (2006.01) | |
| *H01J 37/28* | (2006.01) | |

(52) U.S. Cl.
CPC ............. *H01J 37/261* (2013.01); *G01N 1/28* (2013.01); *G01N 1/286* (2013.01); *H01J 37/304* (2013.01); *G01N 23/2251* (2013.01); *H01J 37/20* (2013.01); *H01J 37/28* (2013.01); *H01J 2237/20207* (2013.01); *H01J 2237/31745* (2013.01); *H01J 2237/31749* (2013.01)

(58) Field of Classification Search
CPC .......... H01J 2237/31745; H01J 37/304; H01J 37/261; G01N 1/286

USPC ................................ 250/311, 310, 307, 304
See application file for complete search history.

(56) References Cited

U.S. PATENT DOCUMENTS

| 5,525,806 A * | 6/1996 | Iwasaki .................... G01N 1/32 250/310 |
| 5,656,811 A * | 8/1997 | Itoh ......................... G01N 1/32 250/310 |
| 6,080,991 A * | 6/2000 | Tsai ......................... 250/492.21 |
| 2002/0079463 A1* | 6/2002 | Shichi ................ B23K 15/0006 250/492.1 |

(Continued)

FOREIGN PATENT DOCUMENTS

JP 04076437 3/1992

*Primary Examiner* — Wyatt Stoffa
*Assistant Examiner* — James Choi
(74) *Attorney, Agent, or Firm* — Adams & Wilks (57) ABSTRACT

A FIB is irradiated onto a sample to form a lamella whose upper side has a thickness of 100 nm or less and whose lower side has a thickness greater than that of the upper side. First and second measurement regions are set on an observation image of the lamella on the upper and lower sides, respectively, where the lamella is thin enough to transmit therethrough an EB. An EB is irradiated onto the first and second measurement regions and charged particles generated therefrom are detected, and a slant angle of one degree or smaller is calculated based on the detected amount of charged particles generated from the first and second measurement regions and the distance between the two regions. The lamella is slanted with respect to the FIB and then irradiated by the FIB by the calculated slant angle to uniformize the thickness of the lamella to a value of 100 nm or smaller.

11 Claims, 8 Drawing Sheets

(56) References Cited

U.S. PATENT DOCUMENTS

| | | | |
|---|---|---|---|
| 2003/0074156 A1* | 4/2003 | Ikeda et al. ................... | 702/137 |
| 2006/0157341 A1 | 7/2006 | Fujii ........................ | 204/192.34 |
| 2007/0221843 A1* | 9/2007 | Ward et al. .................. | 250/309 |
| 2008/0067384 A1 | 3/2008 | Ikku et al. ................... | 250/310 |
| 2008/0191151 A1* | 8/2008 | Shichi ............... | B23K 15/0006 |
| | | | 250/492.3 |
| 2010/0116977 A1* | 5/2010 | Young et al. .............. | 250/252.1 |
| 2010/0300873 A1* | 12/2010 | Blackwood ............. | G01N 1/32 |
| | | | 204/192.33 |
| 2011/0226948 A1* | 9/2011 | Tanaka et al. ................ | 250/307 |
| 2013/0175445 A1* | 7/2013 | Kim ........................ | H01J 37/08 |
| | | | 250/310 |
| 2013/0186747 A1* | 7/2013 | Schmidt ................ | G01N 1/286 |
| | | | 204/192.33 |
| 2013/0328246 A1* | 12/2013 | Wells ...................... | G01N 1/32 |
| | | | 264/400 |

* cited by examiner

FIG. 8B

METHOD FOR PREPARING LAMELLA

BACKGROUND OF THE INVENTION

1. Field of the Invention

The present invention relates to a lamella preparation method and a lamella preparation apparatus for preparing a lamella by etching processing using a focused ion beam.

2. Description of the Related Art

Conventionally, TEM observation is known as a method of observing a microscopic region in a sample for the purpose of analyzing a defect in a semiconductor device or the like. In the TEM observation, in order to obtain a transmission electron image, as preprocessing, it is necessary to process a sample into a lamella having a thickness through which an electron beam may transmit.

In recent years, as a method of preparing a lamella, a lamella preparation method using a focused ion beam is used. In this method, etching processing of peripheral portions of a sample is performed so as to leave a portion in the sample including a region of which observation is desired. Then, etching processing of the remaining portion is performed until the portion has a thickness through which an electron beam may transmit to prepare the lamella. This enables preparation of a lamella precisely including the region of which the observation is desired.

By the way, in the TEM observation, it is desired that the thickness be uniform throughout the lamella. When the thickness is nonuniform, the nonuniformity affects a TEM image and information of the defect and the effect of the nonuniformity in thickness cannot be separated, which causes the analysis to be difficult.

However, a focused ion beam has a certain beam density distribution due to the nature thereof, and thus, when a lamella is prepared by irradiating a focused ion beam from a surface side of a sample, the lamella is tapered, which means the thickness of the lamella is nonuniform.

As a method for solving such a problem, there is disclosed a method of preparing a lamella having a vertical thin wall by etching processing with the sample being slanted taking into consideration the beam density distribution of the focused ion beam (see Japanese Patent Application Laid-open No. Hei 4-76437). According to this method, a lamella having a uniform thickness irrespective of the beam density distribution of the focused ion beam may be prepared.

However, in recent years, as the density of semiconductor devices becomes higher and as the dimensions of a semiconductor device become smaller, the size of a defect which is a target of TEM observation also becomes smaller. In order to make the TEM observation of a microscopic defect with accuracy, it is necessary for the thickness of the lamella to be extremely small.

In conventional lamella preparation, in an apparatus including both a focused ion beam column and an electron beam column, SEM observation of both a front surface and a rear surface of a lamella is made to confirm the shape of the processed lamella. However, in the conventional method involving merely obtaining a SEM image and confirming nonuniformity in thickness by the contrast in the SEM image, when the thickness of the lamella is extremely small, the difference in contrast is small, and thus, it is difficult to confirm the nonuniformity in thickness.

Even if nonuniformity in thickness may be confirmed by the SEM observation, the slant angle of the sample stage necessary for processing for uniform thickness is unknown, and thus, an operator performs the processing while adjusting the slant angle. Such a method depends on the skill of the operator, and thus, it is difficult to secure a certain level of quality.

SUMMARY OF THE INVENTION

The present invention has been made in view of the above-mentioned circumstances, and the present invention provides a lamella preparation apparatus and a lamella preparation method capable of preparing a lamella having a uniform thickness without depending on the skill of an operator.

(1) According to an exemplary embodiment of the present invention, there is provided a lamella preparation apparatus for preparing a lamella by performing processing of a sample using a focused ion beam irradiated from a focused ion beam column, the lamella preparation apparatus including: a sample stage for mounting the lamella thereon; an electron beam column for irradiating an electron beam onto the lamella; a charged particle detector for detecting charged particles released from the lamella by irradiation of the electron beam; and a display unit for displaying an observation image of the lamella formed using a detection signal from the charged particle detector. The lamella preparation apparatus according to the exemplary embodiment of the present invention further includes: an input unit for setting a first measurement region on an upper side and a second measurement region on a lower side of the lamella in the observation image; and a slant angle calculating unit for calculating a slant angle of the lamella from a detected amount of the charged particles generated from the first measurement region and a detected amount of the charged particles generated from the second measurement region by irradiation of the electron beam and a distance between the first measurement region and the second measurement region.

This enables calculation of the slant angle of the lamella with accuracy. Therefore, by processing the lamella using an ion beam under a state in which a sample stage is slanted by the calculated slant angle with respect to the ion beam, a lamella having a uniform thickness may be prepared.

(2) According to the exemplary embodiment of the present invention, there is also provided a lamella preparation method of preparing a lamella by performing processing of a sample using a focused ion beam, the lamella preparation method including: irradiating an electron beam onto the lamella to form an observation image; setting a first measurement region on an upper side and a second measurement region on a lower side of the lamella in the observation image; irradiating the electron beam onto the first measurement region and the second measurement region and detecting charged particles generated there from; calculating a slant angle of the lamella from a detected amount of the charged particles generating from the first measurement region, a detected amount of the charged particles generated from the second measurement region, and a distance between the first measurement region and the second measurement region; slanting the lamella with respect to the focused ion beam by the calculated slant angle; and irradiating the focused ion beam onto the lamella to perform finish processing.

The present invention has an action and effect that the slant angle may be estimated, in particular, even when the slant angle of the lamella is small and a beam is irradiated from a direction perpendicular to a surface of the sample, that is, from a direction within an observation surface of the lamella, and thus, it is difficult to measure the slant angle from the obtained observation image.

According to the lamella preparation apparatus and the lamella preparation method of the exemplary embodiment of the present invention, a lamella having a uniform thickness may be prepared without depending on the skill of an operator.

DETAILED DESCRIPTION OF THE PREFERRED EMBODIMENT

A lamella preparation apparatus and a lamella preparation method according to an embodiment of the present invention are described in the following.

Figure 1:
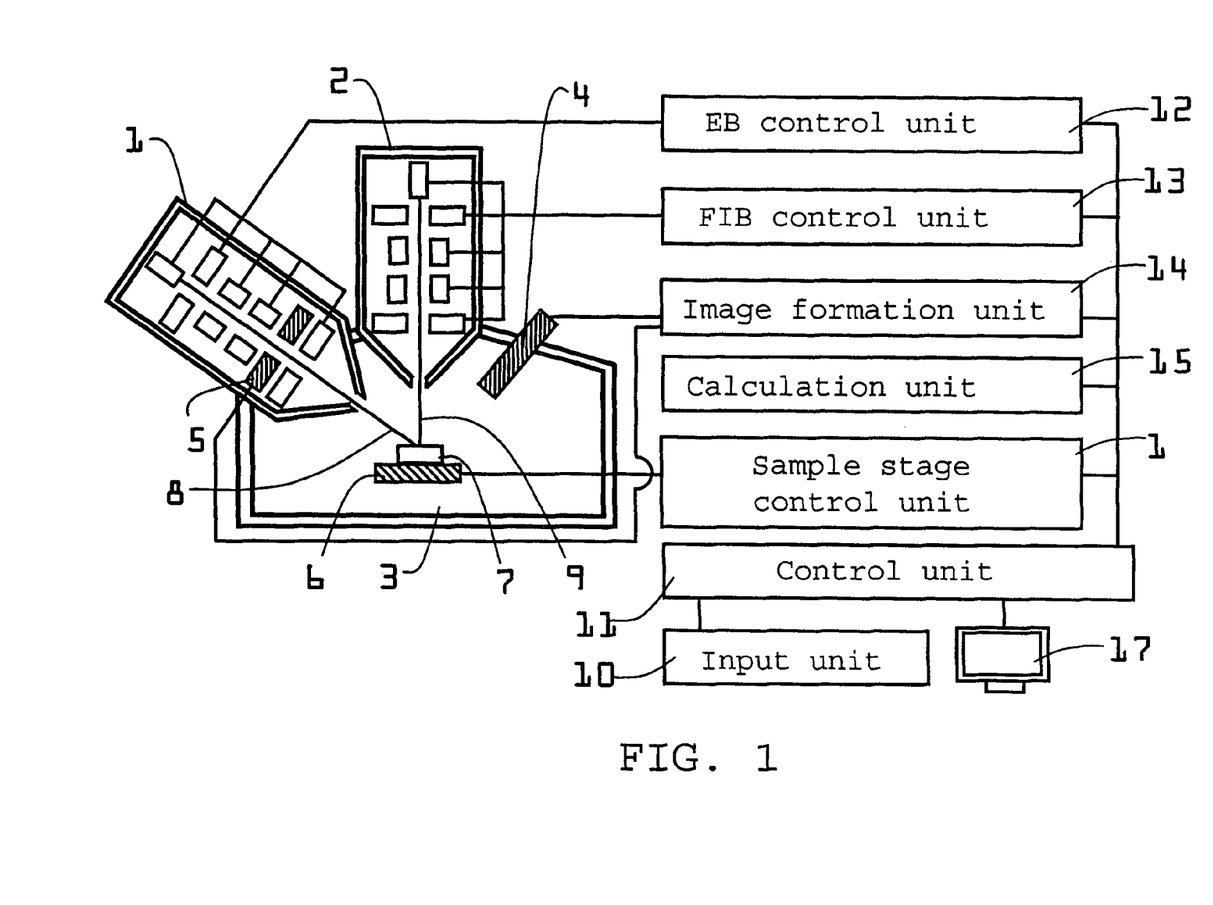
FIG. 1 is a view illustrating the configuration of a lamella preparation apparatus according to an embodiment of the present invention.

As illustrated in FIG. 1, the lamella preparation apparatus of this embodiment includes an EB column 1, an FIB column 2, and a sample chamber 3. An electron beam 8 from the EB column 1 and an ion beam 9 from the FIB column 2 may be irradiated onto a sample 7 housed in the sample chamber 3.

The lamella preparation apparatus further includes a secondary electron detector 4 and a reflected electron detector 5 as charged particle detectors. The secondary electron detector 4 may detect secondary electrons generated from the sample 7 by irradiation of the electron beam 8 or the ion beam 9. The reflected electron detector 5 is provided in the EB column 1. The reflected electron detector 5 may detect electrons reflected by the sample 7 as a result of irradiation of the electron beam 8 onto the sample 7.

The lamella preparation apparatus further includes a sample stage 6 for mounting the sample 7 thereon. By slanting the sample stage 6, the incident angle of the ion beam 9 on the sample 7 may be changed. The sample stage 6 is controlled by a sample stage control unit 16.

The lamella preparation apparatus further includes an EB control unit 12, an FIB control unit 13, an image formation unit 14, and a display unit 17. The EB control unit 12 controls irradiation of the electron beam 8 from the EB column 1. The FIB control unit 13 controls irradiation of the ion beam 9 from the FIB column 2. The image formation unit 14 forms a reflected electron image from a signal for scanning the electron beam 8 of the EB control unit 12 and a signal of reflected electrons detected by the reflected electron detector 5. The display unit 17 may display the reflected electron image. Further, the image formation unit 14 forms a SEM image from the signal for scanning the electron beam 8 of the EB control unit 12 and a signal of secondary electrons detected by the secondary electron detector 4. The display unit 17 may display the SEM image. Further, the image formation unit 14 forms a SIM image from a signal for scanning the ion beam 9 of the FIB control unit 13 and the signal of secondary electrons detected by the secondary electron detector 4. The display unit 17 may display the SIM image.

The lamella preparation apparatus further includes an input unit 10 and a control unit 11. An operator inputs to the input unit 10 conditions with regard to control of the apparatus. The input unit 10 sends input information to the control unit 11. The control unit 11 sends a control signal to the EB control unit 12, the FIB control unit 13, the image formation unit 14, the sample stage control unit 16, or the display unit 17 to control the apparatus.

With regard to control of the apparatus, an operator sets an irradiation region of the ion beam 9 based on, for example, an observation image such as a reflected electron image, a SEM image, or a SIM image displayed on the display unit 17. An operator inputs using the input unit 10 a processing frame for setting the irradiation region on the observation image displayed on the display unit 17. Further, an operator inputs an instruction to start processing to the input unit 10. Then, a signal for indicating the irradiation region and a signal for starting processing are sent from the control unit 11 to the FIB control unit 13, and the ion beam 9 is irradiated from the FIB control unit 13 onto the specified irradiation region of the sample 7. This enables irradiation of the ion beam 9 onto the irradiation region specified by the operator.

Figure 2A:
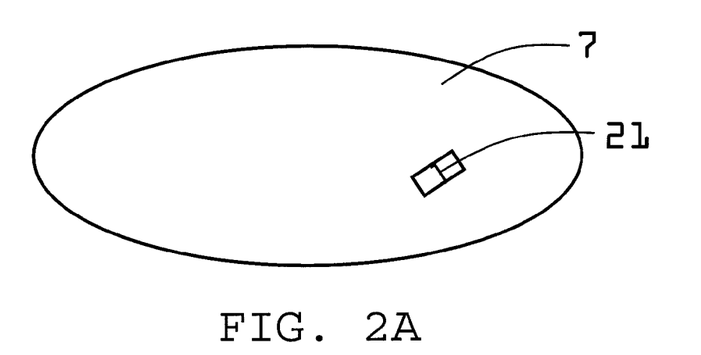
FIG. 2A is an explanatory diagram of lamella preparation according to the embodiment of the present invention.
Figure 2B:
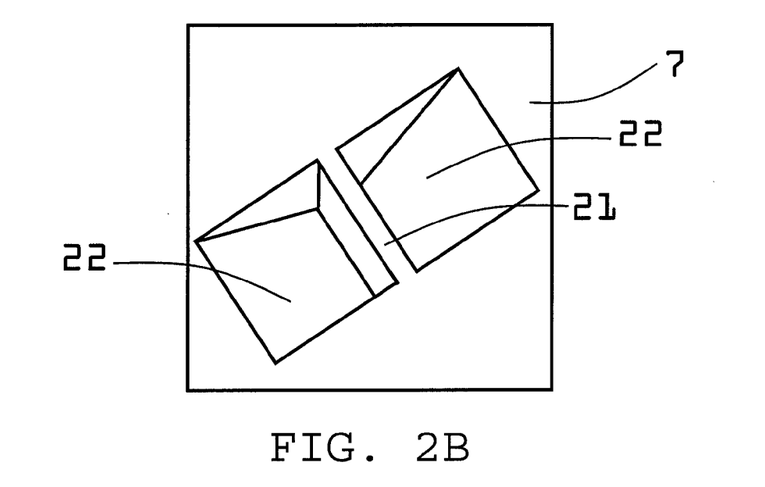
FIG. 2B is an enlarged view of a vicinity of a lamella.
Figure 2C:
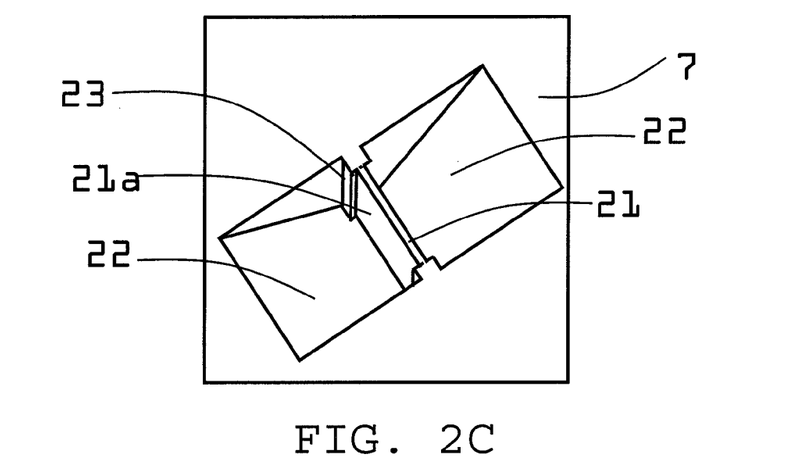
FIG. 2C is another enlarged view of the vicinity of the lamella.

As illustrated in FIG. 2A, the lamella preparation apparatus of this embodiment may prepare a lamella 21 by performing processing of a part of the sample 7 using the ion beam 9. FIG. 2B is an enlarged view of the vicinity of the lamella. The ion beam 9 is irradiated onto the sample 7 to form a processing groove 22 so as to leave the lamella 21. At this stage, the lamella 21 has a thickness through which the electron beam 8 does not transmit. Further, as illustrated in FIG. 2C, by performing thinning processing of the lamella 21 using the ion beam 9, the lamella 21 may have a thickness through which the electron beam 8 may transmit. In this case, a portion 23 which does not undergo the thinning processing has a thickness through which the electron beam 8 cannot transmit. Specifically, the lamella 21 having a thickness through which the electron beam 8 may transmit and a portion having a thickness through which the electron beam 8 cannot transmit may be formed in a part of the sample 7.

Figure 3A:
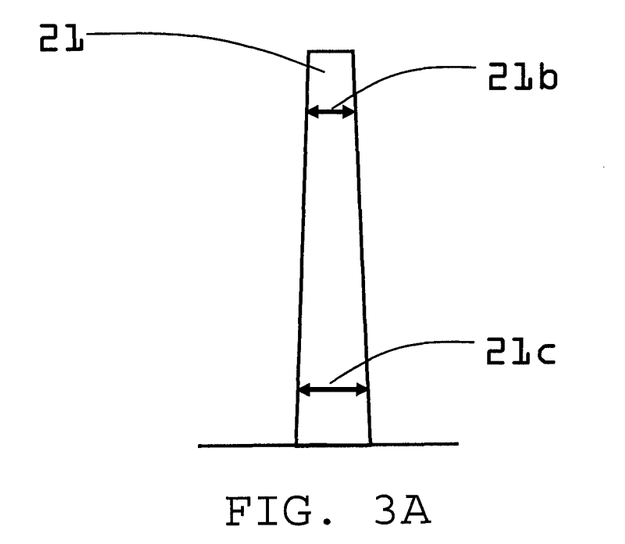
FIG. 3A is a cross-sectional view of the lamella according to the embodiment of the present invention.

By the way, as illustrated in FIG. 3A, the lamella 21 formed by the thinning processing using the ion beam 9 has a small thickness 21*b* on an upper side which is the FIB column 2 side of the lamella 21 (on a distal end side of the lamella 21) and a large thickness 21*c* on a lower side which is the sample stage 6 side (on a proximal end side of the lamella 21). The reason for this is that the current density of the ion beam 9 has a Gaussian distribution, which affects the lamella 21 processed using the ion beam 9 to taper the lamella 21.

Figure 3B:
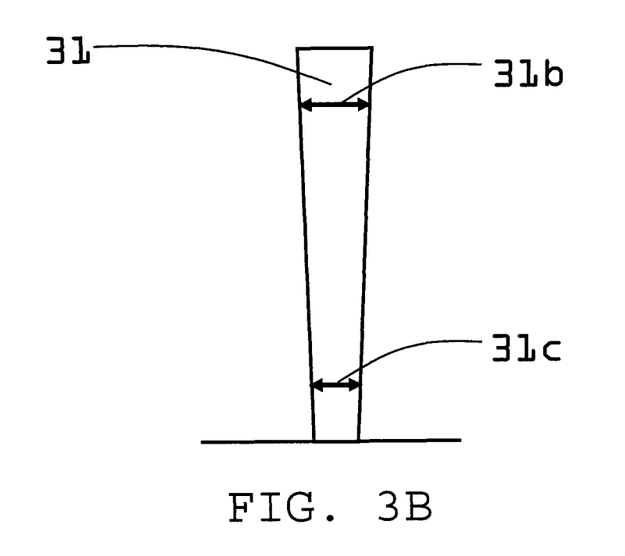
FIG. 3B is another cross-sectional view of the lamella according to the embodiment of the present invention.

In order to make high-resolution TEM observation, the thickness of the lamella 21 which is the target of the observation is desired to be uniform. Therefore, the sample stage 6 is slanted with respect to the ion beam 9 so as to prevent a tapered shape. However, when the slant angle of the sample stage 6 is large, as illustrated in FIG. 3B, the lamella 31 may have a reversed tapered shape in which a thickness 31b on the upper side is large and a thickness 31c on the lower side is small.

In particular, when a lamella having a thickness of 100 nm or smaller is prepared in order to make the high-resolution TEM observation, for the purpose of causing the extent of the taper to be small, finish processing is performed using an ion beam with a small current amount so that the current density distribution of the ion beam is narrow. In this case, the slant angle of the tapered shape, that is, the slant angle of the lamella 21 is one degree or smaller, which is extremely small. Therefore, it is difficult to recognize the slant angle, and thus, conventionally, it follows that operation for slanting the sample stage 6 to adjust the angle of irradiation of the ion beam depends on the skill of an operator.

On the other hand, the lamella preparation apparatus of this embodiment includes a calculation unit 15 for calculating an optimum slant angle of the sample stage 6, and thus, even when the slant angle is one degree or smaller, the sample stage 6 may be slanted to form an optimum slant angle and the lamella 21 having a uniform thickness may be prepared.

Figure 4:
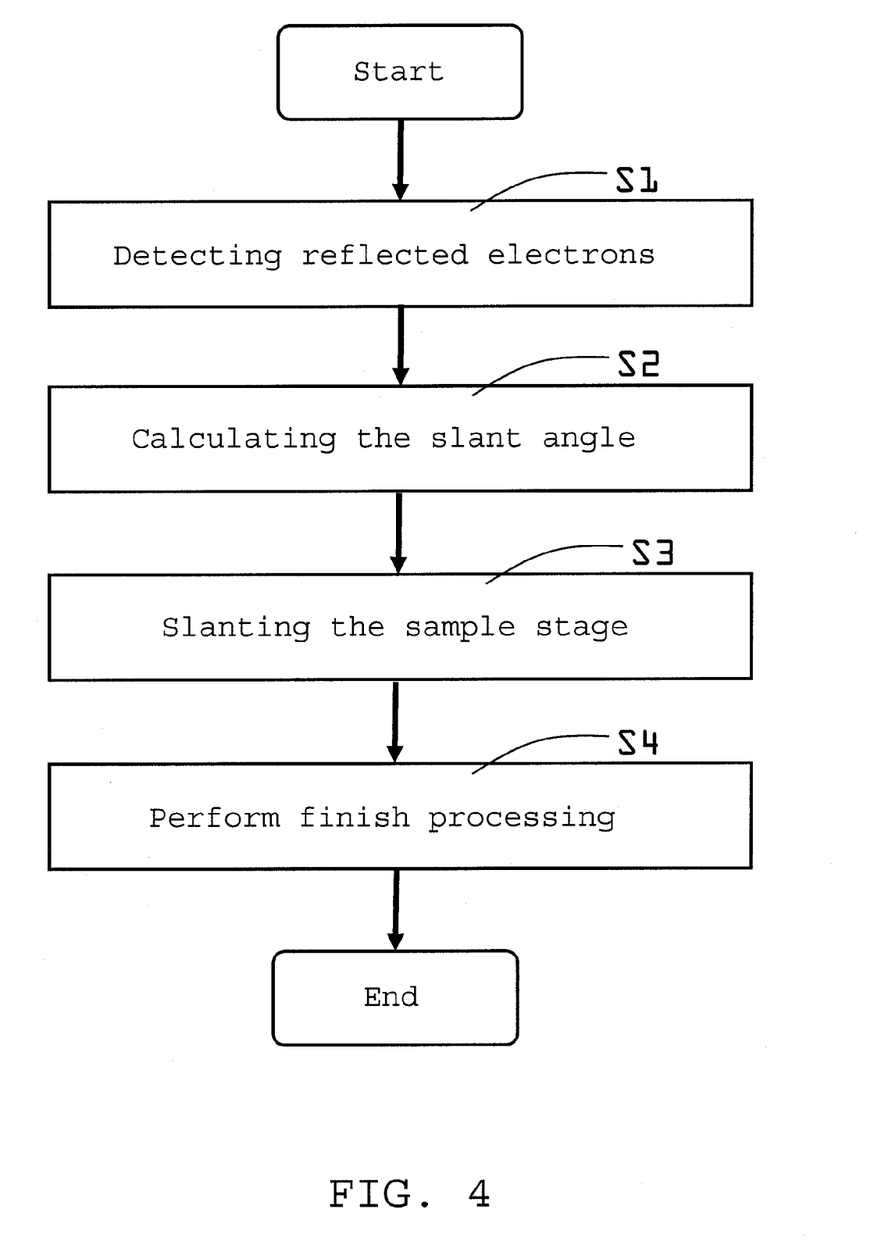
FIG. 4 is a flow chart illustrating a lamella preparation method according to the embodiment of the present invention.

FIG. 4 is a flow chart illustrating a lamella preparation method of this embodiment. First, the electron beam 8 is irradiated onto the lamella 21 formed by the thinning processing, and reflected electrons generated from a measurement region of the lamella 21 are detected (S1). Then, using the detected information, the slant angle of the sample stage 6 is calculated (S2). After that, the sample stage 6 is slanted so that the slant angle becomes a calculated angle (S3). Finally, the ion beam 9 is irradiated onto the lamella 21 to perform finish processing (S4). In this way, the lamella 21 having a uniform thickness may be prepared.

Figure 5A:
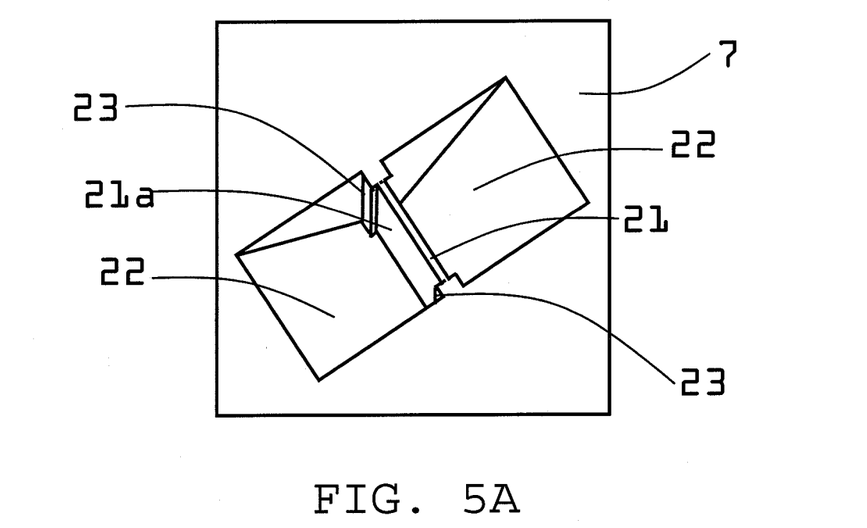
FIG. 5A is an explanatory diagram of lamella preparation according to the embodiment of the present invention.

In the lamella preparation apparatus of this embodiment, reflected electrons are detected as follows. As illustrated in FIG. 5A, the lamella 21 having a thickness through which the electron beam 8 may transmit and a portion having a thickness through which the electron beam 8 cannot transmit are formed in a part of the sample 7. In this case, the sample stage 6 is located so that the ion beam 9 is vertically incident on the surface of the sample 7. Further, the sample 7 is located so that the electron beam 8 may scan and irradiate an observation surface 21a of the lamella 21.

Figure 5B:
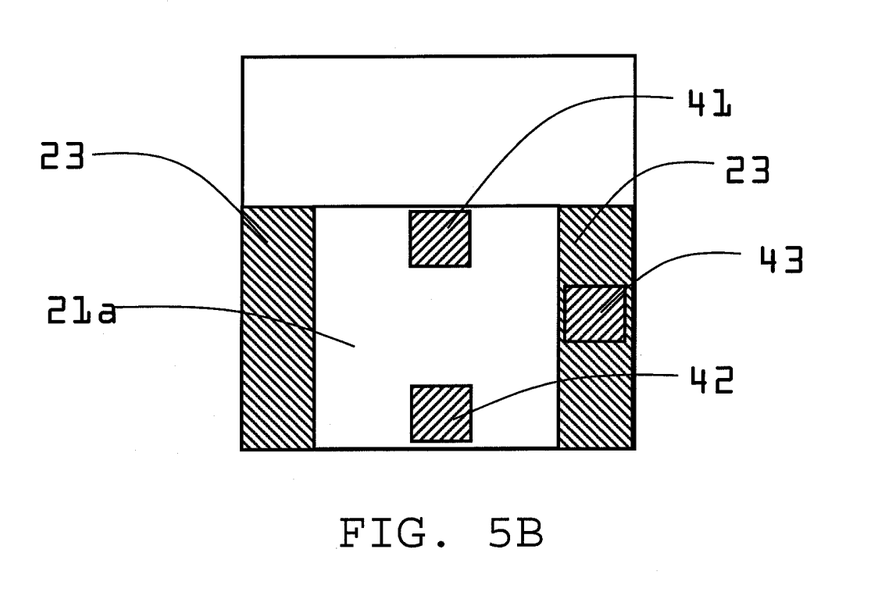
FIG. 5B is a SEM image of an observation surface.

FIG. 5B is a SEM image obtained by scanning and irradiation of the observation surface 21a using the electron beam 8. An operator sets measurement regions 41 and 42 on the upper side and the lower side, respectively, of the observation surface 21a based on the SEM image. As shown, the measurement regions 41,42 are set on the observation surface 21a at locations where the lamella has a thickness through which the electron beam 8 may transmit. Stated otherwise, the measurement regions 41,42 are located where the lamella is thin enough to transmit therethrough the electron beam 8. Further, an operator sets a reference region 43 in the portion 23 which does not undergo the thinning processing. Then, the electron beam 8 is irradiated onto the measurement regions 41 and 42 and the reference region 43 and reflected electrons are detected.

Figure 6:
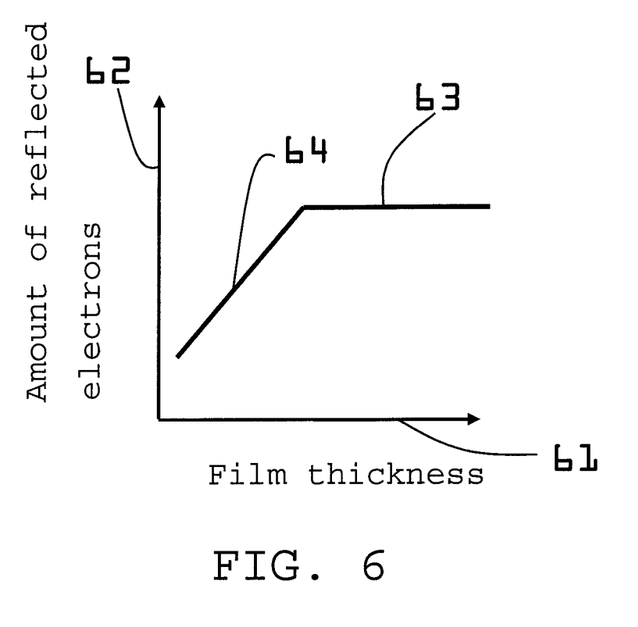
FIG. 6 is a graph showing the relationship between the film thickness and the amount of reflected electrons according to the embodiment of the present invention.

FIG. 6 is a graph showing the relationship between the film thickness and the amount of reflected electrons. In FIG. 6, a horizontal axis 61 denotes the film thickness while a vertical axis 62 denotes the amount of reflected electrons measured in the measurement region. When the film thickness is large, an amount of reflected electrons 63 almost does not change even when the film thickness changes. On the other hand, when the film thickness is small, as the film thickness becomes smaller, an amount of reflected electrons 64 becomes smaller. The reason is that, when the film thickness is small, an amount of electrons which transmit through the lamella 21 of the electron beam 8 irradiated onto the measurement region increases and the amount of reflected electrons decreases. The lamella preparation apparatus of this embodiment irradiates the electron beam 8 onto the measurement regions 41 and 42 and measures the amount of reflected electrons generated from each of the regions.

It is more desired to standardize the amounts of reflected electrons detected in the measurement regions 41 and 42 using the amount of reflected electrons detected in the reference region 43. The reason is that the amount of reflected electrons depends on an amount of the irradiated electron beam 8, and the current amount of the electron beam 8 may fluctuate every time the measurement is made. Therefore, in order to make an accurate measurement, the electron beam 8 is irradiated onto the measurement regions 41 and 42 and the reference region 43, and the amounts of reflected electrons in the measurement regions 41 and 42, respectively, are divided by the amount of reflected electrons in the reference region 43 having a thickness through which the electron beam 8 does not transmit. By using such figures, the measurement of the amounts of reflected electrons may be free from the effect of fluctuations in the amount of the irradiated electron beam 8.

By obtaining in advance preliminary data with regard to the relationship between the amount of reflected electrons and the film thickness using a sample the thickness of which is known and comparing the data with the amounts of reflected electrons in the measurement regions 41 and 42, the thicknesses of the measurement regions 41 and 42 may be estimated.

Figure 7:
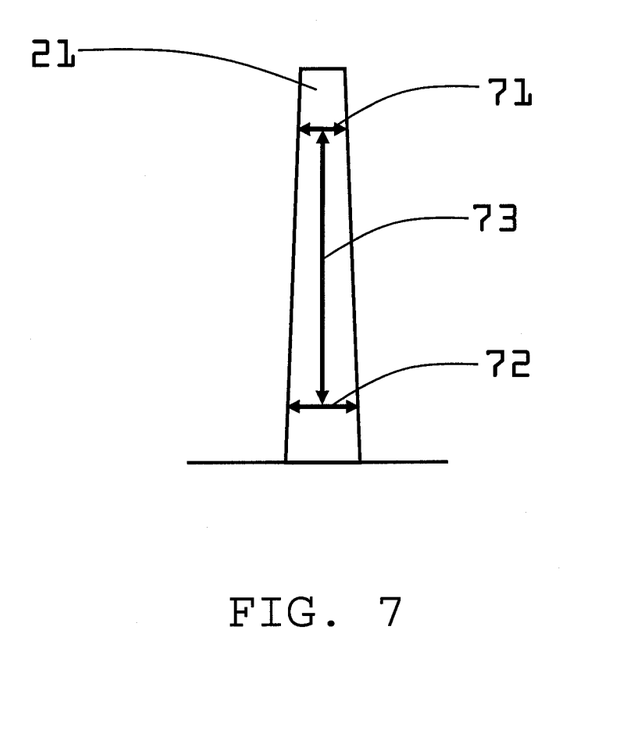
FIG. 7 is a cross-sectional view of the lamella according to the embodiment of the present invention.

FIG. 7 is a cross-sectional view of the lamella 21. When a thickness 71 of the measurement region 41 and a thickness 72 of the measurement region 42 are the same, the amount of reflected electrons in the measurement region 41 and the amount of reflected electrons in the measurement region 42 are the same. When the lamella 21 has a tapered shape as illustrated in FIG. 7, the amount of reflected electrons in the measurement region 41 is smaller than the amount of reflected electrons in the measurement region 42. From this difference and a distance 73 between the measurement region 41 and the measurement region 42, the taper angle which is the slant angle of the lamella 21 may be calculated.

Figure 8A:
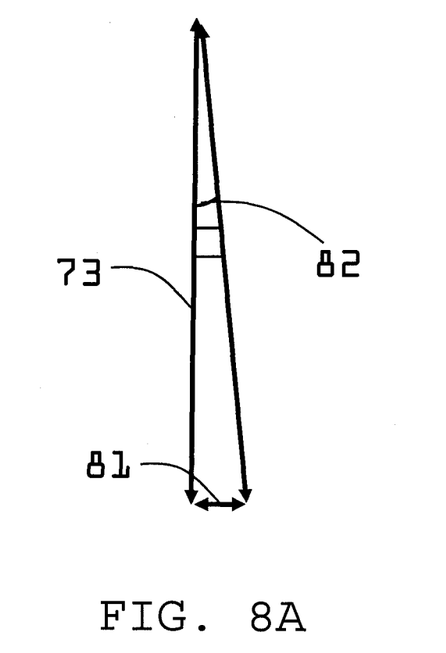
FIG. 8A is an explanatory diagram of a taper angle according to the embodiment of the present invention.

Specifically, as illustrated in FIG. 8A, the relationship between the distance 73 and a taper angle θ formed between a difference 81 between the thickness 71 and the thickness 72 and a line segment 82 of the tapered portion is expressed as tan θ=(difference 81 between thickness 71 and thickness 72)/distance 73, where the distance 73 between the measurement region 41 and the measurement region 42 is the distance between the center of the measurement region 41 and the center of the measurement region 42.

For example, when the thickness 71 is 100 nm, the thickness 72 is 150 nm, and the distance 73 is 3 µm, it follows from the above relational expression that θ is 0.47 degrees.

Figure 8B:
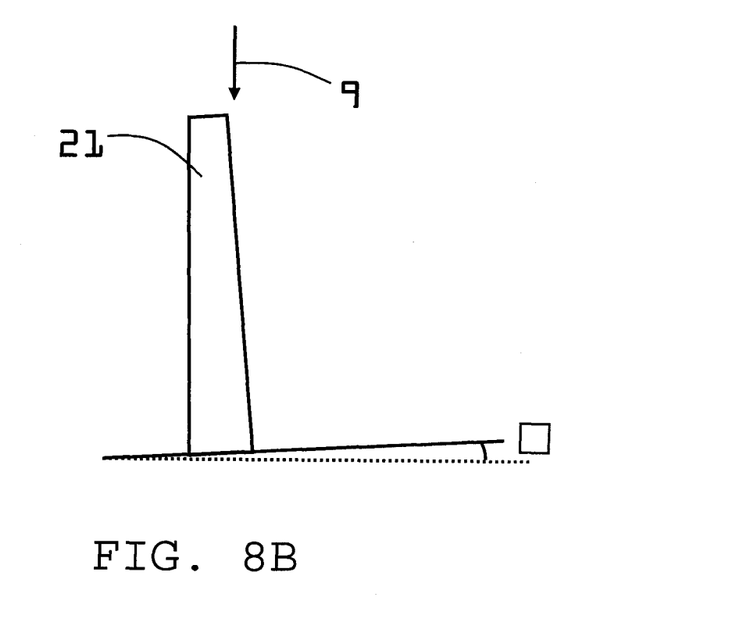
FIG. 8B is an explanatory diagram of finish processing.

As illustrated in FIG. 8B, by slanting the sample stage 6 with respect to the ion beam 9 by θ degrees, one surface of the lamella 21 may be set to be in parallel with the ion beam 9. By performing processing of another surface of the lamella 21 using the ion beam 9 while maintaining this state, the lamella 21 having a uniform thickness may be prepared.

In the above-mentioned embodiment, an example in which reflected electrons are used is described, but, instead of the reflected electrons, secondary electrons generated from the measurement regions 41 and 42 and the reference region 43 may be used.

What is claimed is:

1. A lamella preparation method of preparing a lamella having a thickness of 100 nm or smaller by performing processing of a sample using a focused ion beam, the lamella preparation method comprising:
    irradiating a focused ion beam onto a sample to form a lamella having an upper side having a thickness of 100 nm or smaller and a lower side having a thickness larger than that of the upper side;
    irradiating an electron beam onto the lamella to form an observation image;
    setting a first measurement region on the upper side of the lamella and a second measurement region on the lower side of the lamella in the observation image, the first and second measurement regions being set at locations where the lamella is thin enough to transmit therethrough the electron beam;
    irradiating the electron beam onto the first measurement region and the second measurement region and detecting charged particles generated therefrom;
    calculating a slant angle of the lamella of one degree or smaller based on (a) a difference between the thickness of the first measurement region, which is estimated from a detected amount of the charged particles generated from the first measurement region, and the thickness of the second measurement region, which is estimated from a detected amount of the charged particles generated from the second measurement region, and (b) the distance between the first measurement region and the second measurement region;
    slanting the lamella with respect to the focused ion beam by the slant angle so that a first surface of the lamella is parallel with an irradiation axis of the focused ion beam; and
    irradiating the focused ion beam onto a second surface of the lamella, which is opposite to the first surface, to perform finish processing to uniformize the thickness of the lamella to a value of 100 nm or smaller.

2. A lamella preparation method according to claim 1, further comprising setting a reference region that is in a vicinity of the lamella and that is in a part of the sample having a thickness through which the electron beam does not transmit, irradiating the electron beam onto the reference region, and detecting charged particles generated therefrom,
    wherein the slant angle is calculated by standardizing the detected amount of the charged particles generated from the first measurement region and the detected amount of the charged particles generated from the second measurement region using a detected amount of the charged particles generated from the reference region.

3. A lamella preparation method according to claim 1, wherein the charged particles comprise one of reflected electrons and secondary electrons.

4. A lamella preparation method according to claim 1, wherein the lamella comprises a sample for TEM observation.

5. A lamella preparation method of preparing a lamella having a thickness of 100 nm or smaller by performing processing of a sample using a focused ion beam, the lamella preparation method comprising:
    irradiating a focused ion beam onto a sample to form a lamella having an upper side having a thickness of 100 nm or smaller and a lower side having a thickness larger than that of the upper side;
    irradiating an electron beam onto the lamella to form an observation image;
    setting a first measurement region on the upper side of the lamella and a second measurement region on the lower side of the lamella in the observation image, the first and second measurement regions being set at locations where the lamella is thin enough to transmit therethrough the electron beam;
    irradiating the electron beam onto the first measurement region and the second measurement region and detecting charged particles generated therefrom;
    determining the thickness of the first measurement region based on the detected charged particles generated from the first measurement region and determining the thickness of the second measurement region based on the detected charged particles generated from the second measurement region;
    calculating a slant angle of the lamella of one degree or smaller based on the difference in thickness between the first and second measurement regions and the distance between the first and second measurement regions;
    slanting the lamella with respect to the focused ion beam by the slant angle so that a first surface of the lamella is parallel with an irradiation axis of the focused ion beam; and
    irradiating the focused ion beam onto the a second surface of the lamella, which is opposite to the first surface, to perform finish processing to uniformize the thickness of the lamella to a value of 100 nm or smaller.

6. A lamella preparation method according to claim 5, further comprising setting a reference region that is in a vicinity of the lamella and that is in a part of the sample having a thickness through which the electron beam does not transmit, irradiating the electron beam onto the reference region, and detecting charged particles generated therefrom,
    wherein the slant angle is calculated by standardizing the detected amount of the charged particles generated from the first measurement region and the detected amount of the charged particles generated from the second measurement region using a detected amount of the charged particles generated from the reference region.

7. A lamella preparation method according to claim 5, wherein the charged particles comprise one of reflected electrons and secondary electrons.

8. A lamella preparation method according to claim 5, wherein the lamella comprises a sample for TEM observation.

9. A lamella preparation method according to claim 5, wherein the thicknesses of the first and second measurement regions are determined by comparing the amounts of detected charged particles generated from the first and second measurement regions with the amount of charged particles generated from a reference sample of known thickness when the reference sample is irradiated with an electron beam.

10. A lamella preparation method according to claim 5, wherein in the calculating a slant angle, the distance between the first measurement region and the second measurement region, which have been set in the observation image, is a distance between a center of the first measurement region and a center of the second measurement region as seen from a side of an observation surface of the lamella through which the electron beam is transmitted.

11. A lamella preparation method according to claim 1, wherein in the calculating a slant angle, the distance between the first measurement region and the second measurement region, which have been set in the observation image, is a distance between a center of the first measurement region and a center of the second measurement region as seen from a side of an observation surface of the lamella through which the electron beam is transmitted.

* * * * *